United States Patent [19]

Gemert et al.

[11] Patent Number: 5,066,818

[45] Date of Patent: Nov. 19, 1991

[54] PHOTOCHROMIC NAPHTHOPYRAN COMPOUNDS

[75] Inventors: Barry V. Gemert, Murrsyville, Pa.; Maria P. Bergomi, Akron, Ohio

[73] Assignee: PPG Industries, Inc., Pittsburgh, Pa.

[21] Appl. No.: 490,031

[22] Filed: Mar. 7, 1990

[51] Int. Cl.$^5$ .............................................. C07D 311/92
[52] U.S. Cl. ..................................... 549/389; 549/60; 524/110
[58] Field of Search .................... 524/110; 549/60, 389

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 549/389 |
| 4,215,010 | 7/1980 | Hovey et al. | 252/300 |
| 4,342,668 | 8/1982 | Hovey et al. | 252/586 |
| 4,563,458 | 1/1986 | Widdig et al. | 514/253 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |

FOREIGN PATENT DOCUMENTS

| | | |
|---|---|---|
| 246114 | 5/1987 | European Pat. Off. . |
| 250193 | 6/1987 | European Pat. Off. . |
| 294056 | 12/1988 | European Pat. Off. . |

OTHER PUBLICATIONS

Padwa et al, J. Org. Chem., vol. 40, No. 8, 1975 1142.

*Primary Examiner*—Paul R. Michl
*Assistant Examiner*—Edward J. Cain
*Attorney, Agent, or Firm*—Irwin M. Stein

[57] ABSTRACT

Described are novel reversible photochromic naphthopyran compounds having at least one ortho substituted phenyl group at the 3-position of the pyran ring. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indolino)-oxazine type compounds, are also described.

33 Claims, No Drawings

PHOTOCHROMIC NAPHTHOPYRAN COMPOUNDS

DESCRIPTION OF THE INVENTION

The present invention relates to certain novel naphthopyran compounds. More particularly, this invention relates to novel photochromic naphthopyran compounds, and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −40° C. Irradiation of the compounds with visible light or upon raising the temperature to within the range of −10° C. to 0° C. is reported to reverse the coloration to a colorless state. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

European Patent Publication 246,114 describes a series of photochromic spiropyrans in which an adamantane group is attached at the position adjacent to the oxygen in the pyran ring. U.S. Pat. No. 4,818,096 and European Patent Publication 250,193 describe photoreactive plastic lenses that are coated or impregnated with the photochromic spiropyrans of European Patent Publication 246,114 in combination with a blue photochromic benzopyran or naphthopyran having an aminophenyl substituent at the position adjacent to the oxygen in the pyran ring. European Patent Publication 294,056 describes a process for producing a polyurethane plastic having photochromic properties. Reversible cleavage photochromic compounds disclosed therein include a naphthopyran derivative in which the pyran ring is substituted at the position adjacent to the oxygen in the pyran ring with di(p-methoxyphenyl) substituents.

Padwa et al in J. Org. Chem., Volume 40, No. 8, 1975, page 1142, describes the investigation of photochemical reactions of 2,2-dimethylbenzopyran and related compounds, identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

The present invention relates to certain novel reversible photochromic naphthopyran compounds containing at least one ortho-substituted phenyl substituent at the 3-position of the described pyran ring. These compounds have been found to exhibit a high activated intensity and a reasonable decolorization rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes have been of interest because of the potential safety features that such transparencies offer.

Ideal photochromic compounds for use in optical applications, such as conventional ophthalmic lenses, are those which possess (a) a high quantum efficiency for coloring in the near ultraviolet, (b) a low quantum yield for bleaching with white light and (c) a relatively fast thermal fade at ambient temperature but not so rapid a thermal fade rate that the combination of white light bleaching and thermal fade prevent coloring by the ultraviolet component of strong sunlight.

Compounds, such as 3,3-diphenyl-3H-naphtho[2,1-b]pyran, change color on exposure to the near ultraviolet; but, at room temperature and above, this compound bleaches too rapidly for use in an ophthalmic lens. Substitution of the phenyl ring at the meta and para positions results in an even more rapid bleach rate, and therefore an even lower color intensity. The compound, 2,2-diphenyl-2H-naphthol[1,2-b]pyran, also colors on exposure to near ultraviolet light at room temperature but does not bleach in a reasonable period of time. Substitution of the phenyl substituents in the meta and para positions have little effect on the rate of bleaching of these compounds.

In accordance with the present invention, it has now been discovered that certain novel naphthopyran compounds having a high quantum efficiency for coloring in the near ultraviolet and an acceptable rate of fade may be prepared. These compounds contain at least one ortho-substituted phenyl substituent at the 3-position of the pyran ring, preferably a monoortho-substituted phenyl substituent, and may be graphically represented by the following graphic formula I:

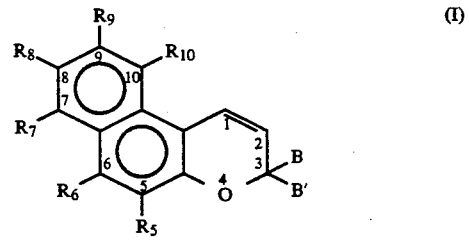

(I)

wherein B may be represented by graphic formula II and B' may be represented by graphic formula III.

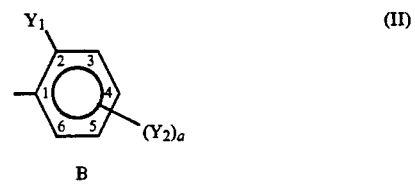

(II)

B

-continued

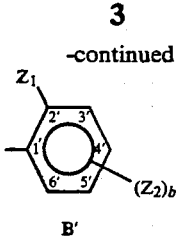

B'    (III)

The novel naphthopyrans of the present invention may be represented graphically also by substituting graphic formulae II and III in formula I, as follows:

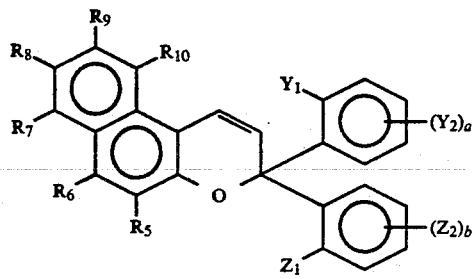

(A-1)

In graphic formula I-A and II, $Y_1$ may be selected from the group consisting of $C_1$–$C_5$ alkyl, $C_1$–$C_5$ alkoxy, fluoro and chloro. Preferably $Y_1$ is selected from the group consisting of $C_1$–$C_3$ alkyl, $C_1$–$C_3$ alkoxy and fluoro. In graphic formula I-A and III, $Z_1$ may be selected from the group consisting of hydrogen and $Y_1$. Each $Y_2$ and $Z_2$ may be selected from the group consisting of $C_1$–$C_5$ alkyl, $C_1$–$C_5$ alkoxy, cyano, hydroxy, halogen, preferably chloro or fluoro, acrylyl, methacrylyl, acryloxy($C_1$–$C_4$) alkyl, and methacryloxy ($C_1$–$C_4$) alkyl. Preferably, each $Y_2$ and $Z_2$ are selected from the group consisting of $C_1$–$C_3$ alkyl, $C_1$–$C_3$ alkoxy and fluoro. The letters a and b in graphic formulae I-A, II and III are each an integer selected from the group consisting of 0, 1 or 2. When a or b are 0 (zero), the phenyl groups of formulae II and III have their appropriate complement of ring hydrogens.

A variety of substituents may be placed on the naphtho portion of the naphthopyran compounds of graphic formula I. For example, the naphtho moiety may be substituted in the positions represented by $R_5$–$R_{10}$ in graphic formula I with $C_1$–$C_{10}$ straight and branched chain alkyl, $C_5$–$C_7$ cycloalkyl, phenyl, mono- or di-substituted phenyl, $C_1$–$C_4$ alkoxy, halogen, i.e. chlorine, fluorine, bromine and iodine, acrylyl, methacrylyl, acryloxy ($C_1$–$C_4$) alkyl, methacryloxy ($C_1$–$C_4$)alkyl, and five or six-membered heterocyclic groups connected to the naphthopyran rings by a single bond, e.g., furyl and thienyl. More particularly, when other than hydrogen, each $R_5$–$R_{10}$ may be $C_1$–$C_5$ straight or branched chain alkyl, e.g., methyl, ethyl, n-propyl, isopropyl, butyl, and pentyl, $C_5$–$C_6$ cycloalkyl, e.g., cyclopentyl and cyclohexyl, $C_1$–$C_3$ alkoxy, e.g., methoxy, ethoxy and propoxy, chlorine (chloro), bromine (bromo), 2- or 3- furyl, 2- or 3-thienyl, phenyl, and ortho-, meta- or para-substituted phenyl. The aforedescribed phenyl substituent(s) each may be selected from the group consisting of $C_1$–$C_4$ alkyl, $C_1$–$C_4$ alkoxy, chloro and bromo. Preferably, the phenyl group is substituted with one substituent and that substituent is in the para position, e.g., p-methyl phenyl, p-chloro phenyl and p-methoxy phenyl. Still more particularly, $R_5$–$R_{10}$ substituents may be $C_1$–$C_3$ alkyl, $C_1$–$C_3$ alkoxy, chloro, bromo, phenyl and $C_1$–$C_3$ alkoxyphenyl, e.g., p-methoxy phenyl.

In naming and referring to the naphthopyran compounds of graphic formula I, positions on the naphthopyran rings are numbered as shown in FIG. 1, e.g., by the numbers appearing on the inside of the rings. As shown in graphic formula I, the naphtho moiety may be substituted at the 5, 6, 7, 8, 9 and/or 10 position, i.e., $R_5$–$R_{10}$. When not so substituted, $R_5$–$R_{10}$ are hydrogen. In certain contemplated embodiments, the naphtho moiety ring is substituted at the 10-position, at the 10- and 9-positions, or the 10- and 6-positions, i.e. $R_{10}$, $R_{10}$ and $R_9$, or $R_{10}$ and $R_6$ respectively. In such embodiments, $R_5$–$R_9$, $R_5$–$R_8$ or $R_7$–$R_9$ and $R_5$ are respectively each hydrogen. In naming the phenyl groups represented by graphic formulae II and III, carbon atom positions are numbered in the manner shown by the numbers appearing on the inside of the phenyl ring.

In a particular embodiment, the naphtho moiety is unsubstituted, i.e., $R_5$–$R_{10}$ are each hydrogen, $Y_1$ is selected from the group consisting of $C_1$–$C_3$ alkyl, $C_1$–$C_3$ alkoxy and fluoro, $Z_1$ is hydrogen, $Y_2$ is $C_1$–$C_3$ alkoxy or hydrogen, $Z_2$ is selected from the group consisting of $C_1$–$C_3$ alkoxy, $C_1$–$C_3$ alkyl and hydrogen, a is 0 or 1 and b is 0, 1 or 2. $Y_2$ and $Z_2$ substituents may be located at any of the unsubstituted positions of their respective phenyl groups; namely positions 3, 4, 5 and 6, preferably at the 3, 4 or 5 positions. When a or b is 1, the substituent is preferably located meta or para to the carbon atom attached to the pyran ring, i.e., the carbon atom identified as position 1( or 1') in graphic formulae II and III. When a and b are 2, the substituents may be located at any two of the unsubstituted carbon atoms of the respective phenyl group; namely positions 3 and 4, 3 and 5, 3 and 6, 4 and 5 or 4 and 6, preferably at the 3 and 4, 3 and 5 or 4 and 5 carbon atoms.

Compounds represented by graphic formula I may be prepared by reaction of the appropriately substituted benzophenone with sodium acetylide in a suitable solvent, such as dry tetrahydrofuran, to obtain the corresponding propargyl alcohol. The propargyl alcohol is then coupled with 2-naphthol under acidic conditions to give the desired naphthopyran. If the starting benzophenone is not commercially available, it may be prepared by a Friedel-Crafts reaction in which the aroyl chloride derivative of graphic formula II is reacted with the appropriately substituted benzene compound of graphic formula III in the presence of a Lewis acid, such as aluminum chloride, and an aprotic solvent, such as carbon disulfide. See, for example, *Friedel-Crafts and Related Reactions*, George A. Olah, Interscience Publishers, 1964, Volume 3, Chapter XXXI (Aromatic Ketone Synthesis).

Compounds represented by graphic formula I may be used in those applications in which organic photochromic substances may be employed, such as for optical lenses, e.g., ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints. Naphthopyrans represented by graphic formula I exhibit color changes from colorless to colors ranging from yellow to orange.

Of particular current interest are the following naphthopyrans:

(1) 3(2-fluorophenyl)-3(4-methoxyphenyl)-3H-naphtho[2,1-b]pyran.

(2) 3(2-fluorophenyl)-3(3,4-dimethoxyphenyl)-3H-naphtho[2,1-b]-pyran.
(3) 3(2-methyl-4methoxyphenyl)-3(4-methoxyphenyl)-3H-naphtho[2,1-b]pyran.
(4) 3(2-methylphenyl)-3(4-methoxyphenyl)-3H-naphtho[2,1-b]pyran.
(5) 3-phenyl-3(2,4-dimethoxphenyl)-3H-naphtho[2,1-b]pyran.
(6) 3(2,6-difluorophenyl)-3(4-methoxyphenyl)-3H-naphtho[2,1-b]-pyran.

Naphthopyrans described herein may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. They may also be dispersed in fluorocarbons and in liquids containing water and/or alcohols.

The aforedescribed naphthopyran compounds may also be dissolved in colorless or transparent solutions prepared from transparent organic host materials, e.g., transparent polymers (homopolymers or copolymers) or blends of such transparent polymers and optionally a suitable organic solvent, e.g., polymers of transparent organic host materials described hereinafter dissolved in one or more of the aforedescribed organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)-acetone solution, a cellulose acetate-dimethylformamide solution, a poly(vinyl pyrrolidone)-acetonitrile solution, a polystyrene-benzene solution and an ethyl cellulose-methylene chloride solution. The aforesaid photochromic solutions or compositions may be applied to a compatible host material, e.g., a transparent support, such as cellulose triacetate, polyethylene terephthalate or baryta paper and dried to obtain an article that will color on exposure to ultraviolet radiation and that will return to its original state by removing the source of ultraviolet radiation.

The naphthopyran compounds described herein (or compositions containing them) may be applied to or incorporated also within a coating composition applied to a compatible support; or applied to or incorporated within the article comprising the compatible host, e.g., a polymerized organic material such as a synthetic polymeric plastic host material.

The naphthopyrans described hereinabove are soluble in synthetic plastic materials customarily used for plastic optical lenses, both plano and ophthalmic, e.g., materials such as methyl methacrylate, polycarbonates and polymerizates prepared from CR-39 ® diallyl glycol carbonate monomer. Photochromic materials for photoreactive lenses preferably have the following stated desirable properties; namely, (a) a high quantum yield for coloring in the near ultraviolet, (b) a low quantum yield for bleaching with visible light, and (c) a fast thermal fade at ambient temperatures, but not so fast that the photochromic material does not color in unfiltered sunlight at ambient temperatures. In addition, the aforesaid properties are desirably retained in conventional rigid synthetic plastic materials customarily used for ophthalmic and plano lenses when such materials have applied to or incorporated therein such naphthopyran compounds.

On irradiation of the compounds of graphic formula I with ultraviolet light, the naphthopyran ring opens reversibly at the carbon-oxygen bond between the number 3-carbon atom and the ring oxygen. The formation of the open form of the colorless compound is believed to be responsible for the coloring observed on exposure to ultraviolet light. The colored form of the photochromic compounds of graphic formula I will fade to the colorless state at normal ambient temperatures when not exposed to ultraviolet light.

Commercially available photoreactive inorganic glass lenses containing silver halide particles darken to a gray or brown color in sunlight. In order to duplicate this color change in a plastic lens using the organic photochromic naphthopyrans of graphic formula I, it is contemplated that such naphthopyrans be used in combination with other appropriate complementary organic photochromic materials so that together they produce the desired gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than photochromic lenses.

Spiro(indolino) pyrido benzoxazine photochromic compounds described in U.S. Pat. No. 4,637,698 and spiro(indolino) naphthoxazines described in U.S. Pat. Nos. 3,562,172, 3,578,602, 4,215,010 and 4,342,668 are reported to color to purple or blue when activated, and these compounds may be used in admixture with or in conjunction with the yellow-orange novel naphthopyran photochromic compounds described in this application to obtain a near gray color when exposed to unfiltered sunlight.

The aforesaid spiro(indolino)-type compounds may be represented by the following graphic formula:

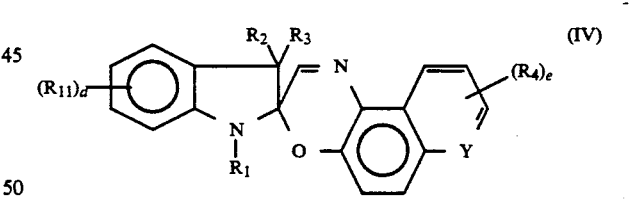

In the above graphic formula IV, $R_1$ is selected from the group consisting of $C_1$-$C_8$ alkyl, e.g., methyl, ethyl, propyl, butyl, etc., phenyl, phen($C_1$-$C_4$)alkyl, e.g., benzyl, naphth($C_1$-$C_4$)alkyl, e.g., 1-naphthylmethyl, allyl, acrylyl($C_2$-$C_6$)alkyl, methacrylyl($C_2$-$C_6$)alkyl, carboxy($C_2$-$C_6$)alkyl, e.g., $\beta$-carboxyethyl, $\gamma$-carboxypropyl, $\delta$-carboxybutyl, cyano ($C_2$-$C_6$)alkyl, e.g., $\beta$-cyanoethyl, $\gamma$-cyanopropyl, $\beta$-cyanoisopropyl, and $\delta$-cyanobutyl, $C_1$-$C_4$ acyloxy($C_2$-$C_6$)alkyl, i.e., [$R_cC(O)OR_d$-, wherein $R_c$ is a $C_1$-$C_4$ alkyl and $R_d$ is a $C_2$-$C_6$ alkyl], e.g., acetoxyethyl, acetoxypropyl, propionyloxyethyl, acetoxybutyl, and propionyloxypropyl, hydroxy($C_2$-$C_6$)alkyl, e.g., hydroxyethyl, hydroxypropyl and hydroxybutyl, $(C_2H_4O)_m \cdot CH_3$, wherein m is a number of from 1 to 6, and mono disubstituted phenyl, said phenyl substituents being selected from $C_1$-$C_4$ alkyl and $C_1-C_5$ alkoxy, e.g., methoxy, ethoxy, propoxy, butoxy and pentoxy. Preferably, $R_1$ is selected from the group consisting of $C_1-C_4$ alkyl, phenyl, benzyl, 1-naphth($C_1-C_2$)alkyl, such as 1-naphthylmethyl, carboxy($C_2-C_4$)alkyl, cyano($C_2-C_4$)alkyl, $C_1-C_4$ acyloxy($C_2-C_4$)alkyl, e.g., $C_1-C_4$ acyloxyethyl, hydroxy($C_2-C_4$)alkyl, and $(C_2H_4O)_m \cdot CH_3$, wherein m is a number of from 1 to 3, e.g., 2.

$R_2$ and $R_3$ of the above graphic formula IV are each selected from the group consisting of $C_1-C_5$ alkyl, phenyl, mono- and disubstituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1-C_4$ alkyl and $C_1-C_5$ alkoxy radicals. More particularly, $R_2$ and $R_3$ are each selected from $C_1-C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

Y in graphic formula IV may be carbon or nitrogen. The number and type of non-hydrogen substituent groups represented by $R_4$ will vary depending upon whether Y is carbon or nitrogen. Generally, when Y is carbon each $R_4$ substituent may be selected from the group consisting of halogen, e.g., chloro, fluoro, or bromo, $C_1-C_5$ alkyl, $C_1-C_5$ alkoxy, e.g., methoxy, ethoxy, propoxy, butoxy and pentoxy, nitro, cyano, thiocyano, $C_1-C_4$ monohaloalkyl, e.g., $C_1-C_4$ monochloroalkyl, such as chloromethyl and chloroethyl, $C_1-C_2$ polyhaloalkyl, as, for example, trihaloalkyl such as trichloroalkyl or trifluoroalkyl, e.g., trifluoromethyl and 2,2,2-trifluoroethyl, and monoalkylamino or dialkylamino wherein the alkyl moiety of the alkylamino group contains between one to four carbon atoms, e.g., methylamino, ethylamino, propylamino, dimethylamino and diethylamino.

The letter "e" in graphic formula IV is an integer of from 0 to 2, e.g., 1, and denotes the number of non-hydrogen substituents. In particular, when "e" is 1 or 2 and Y is carbon, each $R_4$ substituent may be selected from the group $C_1-C_2$ alkyl, $C_1-C_2$ alkoxy, chloro, fluoro, bromo, nitro, and trifluormethyl. When "e" is 0 (zero), there are no non-hydrogen substituents and all of the aromatic carbon atoms have their full complement of hydrogen atoms.

When Y is nitrogen, each $R_4$ non-hydrogen substituent may be selected from $C_1-C_5$ alkyl, e.g., $C_1-C_2$ alkyl, $C_1-C_5$ alkoxy, e.g., $C_1-C_2$ alkoxy, and halogen, e.g., chloro, fluoro or bromo. Typically, "e" is 0 (zero) when Y is nitrogen and thus there are no non-hydrogen substituents.

$R_{11}$ in graphic formula IV may be selected from $C_1-C_5$ alkyl, halogen, $C_1-C_5$ alkoxy, nitro, cyano, $C_1-C_4$ monohaloalkyl, $C_1-C_4$ polyhaloalkyl, $C_1-C_8$ alkoxycarbonyl, $C_1-C_4$ acyloxy, i.e., $R_cC(O)0-$, wherein $R_c$ is a $C_1-C_4$ alkyl, e.g., methyl. The letter "d" in graphic formula IV represents an integer that may vary from 0 to 4, e.g., 0 to 2, such as 1 or 2, and denotes the number of non-hydrogen substituents. When "d" is 0 (zero), there are no non-hydrogen substituents as described with respect to "e".

More particularly, the spiro(indolino) pyridobenzoxazines may be represented by the following graphic formula:

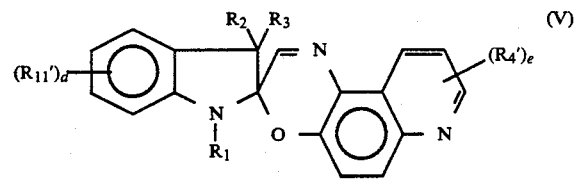

In graphic formula V, $R_1$, $R_2$ and $R_3$ are the same as defined with respect to graphic formula IV. $R'_4$ may be selected from $C_1-C_5$ alkyl, e.g., $C_1-C_2$ alkyl, $C_1-C_5$ alkoxy, e.g., $C_1-C_2$ alkoxy and halogen, e.g., chloro, fluoro or bromo. The letter "e" may be 0 or 1. Commonly, "e" is 0, and thus, there are no non-hydrogen substituents. When "e" is 1, the $R'_4$ substituent may be located on any of the available carbon atoms of the pyrido moiety of the pyridobenzoxazine portion of the compound, i.e., at the 5', 6', 8' 9' or 10' positions, most usually at the 8', 9' or 10' positions.

$R'_{11}$ in graphic formula V may be selected from the group consisting of $C_1-C_5$ alkyl, e.g., methyl, ethyl, propyl, butyl and pentyl, halogen, e.g., chloro and fluoro, $C_1-C_5$ alkoxy, e.g., methoxy, ethoxy, propoxy, butoxy and pentoxy, nitro, cyano, $C_1-C_4$ monohaloalkyl, e.g., chloromethyl, fluoromethyl, chloroethyl, chloropropyl, etc., $C_1-C_4$ polyhaloalkyl, e.g., trihaloalkyl, $C_1-C_8$ alkoxycarbonyl, and $C_1-C_4$ acyloxy, i.e., $R_cC(O)0-$, wherein $R_c$ is a $C_1-C_4$ alkyl, e.g., methyl. An example of an acyloxy group is acetoxy. While any halogen, i.e., chlorine, bromine, iodine and fluorine may be used in respect to the aforesaid halogen or haloalkyl substituents, chlorine, fluorine and bromine, particularly chlorine and fluorine, are preferred for the halogen substituent and fluorine is preferred for the polyhaloalkyl substituent, e.g., trifluoromethyl, $(CF_3)$. Preferably, $R'_{11}$ is selected from the group consisting of $C_1-C_2$ alkyl, chlorine, fluorine, $C_1-C_2$ trihaloalkyl, e.g., trihalomethyl such as trifluoromethyl and $C_1-C_5$ alkoxy.

The letter "d" in graphic formula V is an integer from 0 to 4, e.g., 0 to 2, such as 1 or 2. When "d" is 2 or more, each $R'_{11}$ substituent may be the same or different and in either case, are selected from the aforedescribed group. The $R'_{11}$ substituent(s) may be located on any of the available carbon atoms of the benzene ring of the indolino portion of the compound, i.e., at the 4, 5, 6 or 7 positions. When "d" is 2, the $R'_{11}$ substituents may be present at the 4 and 5, 5 and 6, 4 and 7 or 6 and 7 carbon atoms of the indoline moiety.

It is possible that photochromic organic substances of graphic formula V (and VI) may be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "d" is 1, the photochromic substance may be substituted at the 4 position on the indoline ring, at the 6 position of that ring or comprise a mixture of such isomers. When "d" is 2, the photochromic substance may be substituted at any combination of the 4, 5, 6, or 7 carbon atoms of the indoline ring (as heretofore indicated) and may comprise an isomeric mixture of such compounds, e.g., a mixture of compounds having substituents at the 4 and 5, 4 and 6, 5 and 6, 4 and 7, 5 and 6 and 7 positions of the indoline ring. Commonly, when "d" is 2 the substituents are located at the 4 and 5, or 5 and 6 positions. Also contemplated are materials containing mixtures of such isomers, e.g., materials comprising 4 (and 6) and 5-substituted spiro-(indolino) benzoxazines.

Non-limiting examples of spiro(indolino) pyridobenzoxazines of graphic formula V described in Table 1. Such pyridobenzoxazines are those in which $R_1$, $R_2$, $R_3$, and $R'_{11}$ are as indicated in Table 1, the letter "e" is 0 (zero), and the letter "d" is 0, 1 or 2. A hyphen (-) indicates the absence of a non-hydrogen substituent.

TABLE 1

| Compound | $R_1$ | $R_2$ | $R_3$ | $R_{11}'$ | $R_{11}'$ |
|---|---|---|---|---|---|
| 1 | $CH_3$ | $CH_3$ | $CH_3$ | — | — |
| 2 | $CH_3$ | $CH_3$ | $CH_3$ | 4(6)-$CH_3$ | 5-$CH_3$ |
| 3 | $CH_3$ | $CH_3$ | $CH_3$ | 5-$OCH_3$ | — |
| 4 | $CH_3$ | $CH_3$ | $CH_3$ | 5-Cl | 6-$CH_3$ |
| 5 | $CH_3$ | $CH_3$ | $C_2H_5$ | — | — |
| 6 | $CH_3$ | $CH_3$ | $C_2H_5$ | 5-$CH_3$ | 4(6)-$CH_3$ |
| 7 | $CH_3$ | $C_2H_5$ | $C_2H_5$ | — | — |
| 8 | n-$C_4H_9$ | $CH_3$ | $C_2H_5$ | — | — |
| 9 | $CH_3$ | $CH_3$ | phenyl | — | — |
| 10 | $CH_3$ | phenyl | phenyl | — | — |
| 11 | $C_2H_5$ | $CH_3$ | $C_2H_5$ | 4(6)-$CH_3$ | 5-$CH_3$ |
| 12 | n-$C_4H_9$ | $CH_3$ | $C_2H_5$ | 5-$CH_3$ | 6-$CH_3$ |
| 13 | $CH_3$ | $CH_3$ | $CH_3$ | 5-$CH_3$ | 6-$CH_3$ |
| 14 | n-$C_3H_7$ | $CH_3$ | $CH_3$ | 5-$CH_3$ | — |
| 15 | i-$C_3H_7$ | $CH_3$ | $CH_3$ | 5-$OCH_3$ | — |

Compound 2 in Table 1 may be names 1,3,3,4,5-pentamethylspiro[indolino-2,3' [3H]pyrido [3,2-f][1,4] benzoxazine]. Similarly, compound 6 in Table 1 may be names 1,3,5,6-tetramethyl-3-ethylspiro[indolino-2,3' [3H]pyrido [3,2-f][1,4]benzoxazine]. Other compounds in Table 1 may be similarly named taking into account the different substituents. Moreover, compounds selected from the description of graphic formula V may be similarly named by substituting the substituents described with respect to $R_1$, $R_2$, $R_3$, $R_4$ and $R'_{11}$ for those found in Table 1. When the letter "e" is 1 or more, the $R'_4$ substituent(s) are given a prime (') designation. For nomenclature purposes, numbering of the pyrido benzoxazine portion of the molecule is counter clockwise starting with the nitrogen atom of the oxazine ring as the 1' position. Numbering of the indolino portion of the molecule is counter clockwise starting with the nitrogen atom.

Spiro(indolino)naphthoxazines that may be used in the practice of the present process may be represented by the following graphic formula:

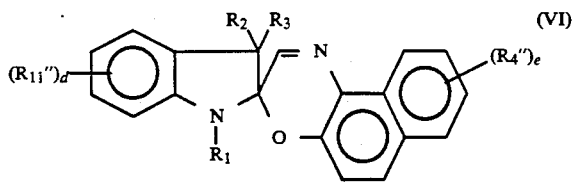

wherein $R_1$, $R_2$ and $R_3$ are the same as that described with respect to graphic formula IV.

Each $R'_{11}$ substituent in graphic formula VI may be selected from the group consisting of halogen, e.g., chloro, fluoro, or bromo, $C_1$-$C_5$ alkyl, $C_1$-$C_5$ alkoxy (e.g., methoxy, ethoxy, propoxy, butoxy and pentoxy), nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhalozlkyl, as for example, trihaloalkyl, such as trichloroalkyl or trifluoroalkyl, e.g., trifluoromethyl and 2,2,2-trifluoroethyl, and monoalkylamino or dialkylamino, wherein the alkyl moiety of the alkylamino group contains from 1 to 4 carbon atoms, e.8., methylamino, ethylamino, propylamino, dimethylamino and diethylamino. More particularly the $R'_{11}$ substituent may be selected from the group $C_1$-$C_2$ alkyl, $C_1$-$C_2$ alkoxy, chloro, fluoro, bromo, nitro and trifluormethyl. The letter "e" in graphic formula VI is an integer from 0 to 2, e.g., 1 or 2, and denotes the number of non-hydrogen substituents. When "e" is 0, all of the substituents on the available carbon atoms of the naphtho moiety of the molecule represented by formula VI are hydrogen.

As in the case with graphic formula V, when "e" is 1, the $R'_4$ substituent may be located on any of the available carbon atoms of the naphtho moiety of the naphthoxazine portion of the molecule, i.e., at the 5', 6', 7' 8', 9' or 10' positions. Preferably, the $R'_4$ substituent is present on the 7', 8' or 9' carbon atoms. When "e" is 2, each of the $R'_4$ substituents may be same or different and in either case are selected from the above-described group. When "e" is 2, the $R'_4$ substituents are commonly located at the 7' and 9', or 8' and 10' positions. For nomenclature purposes, numbering of spiro(indolino) naphthoxazines is the same as that described with regard to the spiro(indolino) pyrido benzoxazines of graphic formula V. $R'_{11}$ and the letter "d" In graphic formula VI are the same as that described with respect to $R_{11}$ and d in graphic formula IV.

Non-limiting examples of spiro(indolino) naphthoxazines selected from the description of graphic formula VI are described in Table 2. Such spiro(indolino) naphthoxazines are those in which $R_1$, $R_2$, $R_3$, $R'_4$ and $R'_{11}$ are as indicated in Table 2, the letter "d" is 0, 1 or 2 and the letter "e" is 1. As in Table 1, a hyphen (-) indicates the absence of a non-hydrogen substituent. In Table 2, all of the $R'_4$ substituents are at the 9' carbon position.

TABLE 2

| Compound | $R_1$ | $R_2$ | $R_3$ | $R_4''$ (9'-) | $R_{11}''$ | $R_{11}''$ |
|---|---|---|---|---|---|---|
| 1 | $CH_3$ | $CH_3$ | $CH_3$ | $OCH_3$ | — | — |
| 2 | $CH_3$ | $CH_3$ | $CH_3$ | $OCH_3$ | 5-$CH_3$ | 6-$CH_3$ |
| 3 | $CH_3$ | $CH_3$ | $CH_3$ | $OCH_3$ | 5-$OCH_3$ | — |
| 4 | $CH_3$ | $CH_3$ | $CH_3$ | $OCH_3$ | 5-Cl | 6-$CH_3$ |
| 5 | $CH_3$ | $CH_3$ | $C_2H_5$ | $OCH_3$ | — | — |
| 6 | $CH_3$ | $CH_3$ | $C_2H_5$ | $OCH_3$ | 5-$CH_3$ | 6-$CH_3$ |
| 7 | $CH_3$ | $C_2H_5$ | $C_2H_5$ | $OCH_3$ | — | — |
| 8 | n-$C_4H_9$ | $CH_3$ | $C_2H_5$ | $OCH_3$ | — | — |
| 9 | $CH_3$ | $CH_3$ | phenyl | $OCH_3$ | — | — |
| 10 | $CH_3$ | phenyl | phenyl | $OCH_3$ | — | — |

TABLE 2-continued

| Compound | R₁ | R₂ | R₃ | R₄″ (9′-) | R₁₁″ | R₁₁″ |
|---|---|---|---|---|---|---|
| 11 | CH₃ | p-C₆H₄OCH₃ | p-C₆H₄OCH₃ | OCH₃ | — | |
| 12 | C₂H₅ | CH₃ | C₂H₅ | OCH₃ | 5-CH₃ | — |
| 13 | n-C₄H₉ | CH₃ | C₂H₅ | OCH₃ | 5-CH₃ | — |

Compound 2 in Table 2 may be named 1,3,3,5,6-pentamethyl-9′-methoxy-spiro [indolino-2,3′ [3H]-naphth [2,1-b] [1,4]oxazine]. Similarly, compound 6 in Table 2 may be named 1,3,5,6-tetramethyl-3-ethyl-9′-methoxyspiro [indolino-2,3′ [3H]-naphth [2,1-b] [1,4]-oxazine. Other compounds in Table 2 can be similarly named taking into account the different substituents. Moreover, compounds selected from the description of graphic formula VI may be similarly named.

Spiro(indolino) benzoxazines compounds described in U.S. Pat. No. 4,816,584 are reported to color to from blue to red when activated and may be used in admixture with or in conjunction with the novel naphthopyran compounds described in this application. The spiro-(indolino) benzoxazines may be represented by the following graphic formula VII.

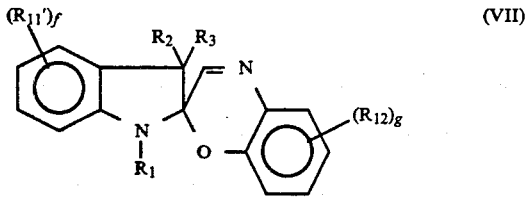

wherein $R_1$, $R_2$, $R_3$ and $R'_{11}$ are the same as described with respect to graphic formula V and $R_{12}$ is selected from the group consisting of halogen, e.g., chloro, fluoro, or bromo, $C_1$-$C_4$ alkyl, e.g., $C_1$-$C_2$ alkyl, $C_1$-$C_5$ alkoxy, e.g., $C_1$-$C_2$ alkoxy, nitro, cyano, thiocyano, $C_1$-$C_4$ monohaloalkyl, e.g., chloromethyl and chloroethyl, $C_1$-$C_2$ polyhaloalkyl, e.g., trihaloalkyl, such as trifluoromethyl and 2,2,2-trifluoroethyl and monoalkylamino or dialkylamino, wherein the alkyl moiety of the alkylamino group contains from 1 to 4 carbon atoms, e.g., methylamino, dimethylamino, and diethylamino. The letter "g" in formula VII is an integer from 1 to 4, usually 1 to 3, more usually 1 or 2. The letter "f" in formula VII is an integer of from 0 to 2, more usually 1 or 2.

When "g" is 1, the $R_{12}$ substituent may be located on any of the available carbon atoms of the benzene ring of the benzoxazine moiety, i.e., at the 5, 6, 7 or 8 positions. Preferably, the $R_{12}$ substituent is located on the 5, 6, or 7 carbon atoms. When "g" is 2 or more, each of the $R_{12}$ substituents may be the same or different and in either case are selected from the above-described group. When "g" is 2, the $R_{12}$ substituents are desirably located at the 5 and 7 or 6 and 8 positions.

Examples of spiro(indolino)benzoxazines within the scope of graphic formula VII are listed in Table 3. Compound 1 may be named: 7-methoxy-1′, 3′, 3′, 4′ (and 6′), 5′-pentamethylspiro[2H-1,4-benzoxazine -2,2-indoline]. Compounds 2–48 may be similarly named as substituted spiro(indolino) benzoxazines using the substituents described in Table 3 for such compounds. In naming the spiro(indoline)benzoxazines, the IUPAC rules of organic nomenclature have been used. The positions of the indolino portion of the molecule have been numbered counterclockwise starting with the nitrogen atom as number one (1), and are identified by a prime number, e.g., 3′. The positions of the benzoxazine portion of the molecule have been numbered clockwise starting with the oxygen atoms as number one (1).

TABLE 3

| Compound No. | SUBSTITUENT | | | | | | |
|---|---|---|---|---|---|---|---|
| | R₁ | R₂ | R₃ | R₁₁′ | R₁₁′ | R₁₂ | R₁₂ |
| 1 | Me | Me | Me | 4(6)-Me | 5-Me | 7-OMe | — |
| 2 | Me | Me | Me | 4(6)-Me | 5-Me | 7-OMe | 5-OMe |
| 3 | Me | Me | Me | 5-OMe | — | 7-OMe | 5-OMe |
| 4 | Me | Me | Me | 4(6)-Me | 5-Me | 7-OMe | 5-Cl |
| 5 | Me | Me | Me | 4(6)-Me | 5-Me | 6-NO₂ | — |
| 6 | Me | Me | Me | 4(6)-Me | 5-Me | 6-Cl | — |
| 7 | Me | Me | Ph | — | — | 7-OMe | — |
| 8 | n-Pr | Me | Et | — | 5-Me | 7-OMe | 5-OMe |
| 9 | n-Bu | Me | Me | — | — | 7-OMe | 5-OMe |
| 10 | Me | Cyclohexyl | | — | — | 7-OMe | 5-OMe |
| 11 | Me | Me | Me | 5-OMe | — | 6-NO₂ | — |
| 12 | Me | Me | Me | 5-OMe | — | 6-NO₂ | 8-OMe |
| 13 | Et | Me | Me | 5-OMe | — | 6-NO₂ | 8-OMe |
| 14 | Me | Me | Et | 4(6)-Me | 5-Me | 6-NO₂ | 8-OMe |
| 15 | Me | Me | Ph | — | — | 6-NO₂ | 8-OMe |
| 16 | Me | Me | Me | 4(6)-Me | 5-Me | 8-NO₂ | 6-OMe |
| 17 | Me | Me | Me | — | — | 8-NO₂ | 6-OMe |
| 18 | Me | Me | Me | 5-OMe | — | 8-NO₂ | 6-OMe |
| 19 | Et | Me | Me | — | — | 7-OMe | 6-Br |
| 20 | n-Pr | Me | Et | 4(6)-Me | 5-Me | 7-OMe | 5-OMe |
| 21 | i-Pr | Me | Me | 5-OMe | — | 7-OMe | 5-OMe |
| 22 | Me | Me | Me | — | — | 7-NEt₂ | — |
| 23 | Benzyl | Me | Me | — | — | 7-NO₂ | — |
| 24 | Me | Me | Me | 4(6)-F | — | 7-OMe | 5-OMe |
| 25 | Me | Me | Me | 6-Cl | — | 7-OMe | 5-OMe |
| 26 | Me | Me | Me | 7-F | — | 7-OMe | 5-OMe |
| 27 | Me | Me | Me | 7-Cl | — | 7-OMe | 5-OMe |
| 28 | Me | Me | Me | 7-Br | — | 7-OMe | 5-OMe |
| 29 | Me | Me | Me | 5-F | — | 7-OMe | 5-OMe |

TABLE 3-continued

| Compound No. | R₁ | R₂ | R₃ | R₁₁' | R₁₁' | R₁₂ | R₁₂ |
|---|---|---|---|---|---|---|---|
| 30 | Me | Me | Me | 5-Cl | — | 7-OMe | 5-OMe |
| 31 | Me | Me | Me | 5-OMe | — | 7-OMe | 5-OMe |
| 32 | Me | Me | Me | 5-OMe | — | 7-OMe | — |
| 33 | Me | Me | Me | 6-CF₃ | — | 7-OMe | 5-OMe |
| 34 | Me | Me | Et | 4(6)-F | — | 7-OMe | 5-OMe |
| 35 | Me | Me | Me | 4(6)AcO | — | 7-OMe | 5-OMe |
| 36 | Me | Me | Me | 4(6)CF₃ | — | 7-OMe | 5-OMe |
| 37 | Me | Me | Me | 4(6)F | 5-F | 7-OMe | 5-OMe |
| 38 | Me | Me | Me | 4(6)Cl | 5-Cl | 7-OMe | 5-OMe |
| 39 | Me | Me | Me | 4(6)F | — | 7-OMe | 5-Cl |
| 40 | Me | Me | Me | 4(6)F | — | 7-OMe | 5-F |
| 41 | Me | Me | Me | 4(6)AcO | — | 7-OMe | 5-OMe |
| 42 | Me | Me | Me | — | 5-AcO | 7-OMe | 5-OMe |
| 43 | Me | Me | Me | 4(6)AcO | 5-F | 7-OMe | 5-OMe |
| 44 | Me | Me | Me | 4(6)AcO | 5-Cl | 7-OMe | 5-OMe |
| 45 | CNPr | Me | Me | — | — | 7-OMe | — |
| 46 | C(O)OEt | Me | Me | — | — | 7-OMe | 5-OMe |
| 47 | (EtO)₂Me | Me | Me | — | — | 7-OMe | — |
| 48 | HOEt | Me | Me | — | — | 7-OMe | — |

Key:
Me = methyl
n-Bu = n-butyl
Et = ethyl
Pr = propyl
CNPr = γcyanoisopropyl
(EtO)₂Me = CH₃OCH₂CH₂OCH₂CH₂—
Ph = phenyl
OMe = methoxy
NO₂ = nitro
NEt₂ diethylamino
C(O)OEt = β-carboxyethyl
Br = bromine
Cl = chlorine
F = fluorine
AcO = acetoxy
HOEt = hydroxyethyl The naphthopyran compounds of the present invention may be combined with spiro(indolino) pyrido benzoxazine or spiro(indolino) naphthoxazine compounds in amounts and in a ratio such that an organic host material to which the mixture of compounds is applied or in which they are incorporated exhibits a substantially neutral color when activated with unfiltered sunlight, i.e., as near a neutral color as possible given the colors of the activated pyran and oxazine photochromic compounds. The relative amounts of the oxazine and pyran compounds used will vary and depend in part upon the relative intensities of the color of the activated species of such compounds. Similarly, the naphthopyran compounds of the present invention may be combined with spiro(indolino)benzoxazine compounds in amounts and in a ratio such that an organic host material to which the mixture of compounds is applied or in which they are incorporated exhibits a near-brown color. Generally, the mole ratio of the aforedescribed spiro(indolino) oxazine compound(s) to the pyran compound(s) of the present invention will vary from about 1:3 to about 3:1, e.g., between about 1:2 and about 2:1.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. For example:

(a) The photochromic substance may be mixed with a polymerizable composition that, upon curing, produces a polymeric host material and the polymerizable composition cast as a film, sheet or lens, injection molded or otherwise formed into a sheet or lens, or polymerized by emulsion or suspension polymerization to form a photochromic particulate material that may be used as a pigment;

(b) The photochromic substance may be dissolved or dispersed in water, alcohol or other solvents or solvent mixtures and then imbibed into the solid host material by immersion of the solid host material for from several minutes to several hours, e.g., 2–3 minutes to 2–4 hours, in a bath of such solution or dispersion. The bath is conventionally at an elevated temperature, usually in the range of 50–120° C.; however, higher temperatures may be used. Thereafter, the host material is removed from the bath and dried;

(c) The photochromic substance may also be applied to the surface of the host material by any convenient manner, such as spraying, brushing, spin-coating or dip-coating from a solution or dispersion of the photochromic substance in the presence of a polymeric binder. Thereafter, the photochromic substance is imbibed into the host material by heating it, e.g., in an oven, for from a minute to several hours, e.g., 2 to 3 hours, at temperatures in the range of from 80–180° C., e.g., 100–150° C.;

(d) In a variation of the preceding imbibition procedure, the photochromic substance may be deposited onto or absorbed by a temporary support, e.g., a sheet of kraft paper, aluminum foil, polymer film or fabric, which is then placed in near proximity to or in contact with the host material and heated, e.g., in an oven. This and the preceding procedure may be repeated one or more times to imbibe the desired amount of photochromic substance into the host material;

(e) The photochromic substance may be dissolved or dispersed in a transparent polymeric material which may be applied to the surface of the host in the form of an adherent film by any suitable technique such as spraying, brushing, spin-coating or dip-coating; and finally (f) The photochromic substance may be incorporated in or applied to a transparent polymeric material by any of the above-mentioned methods, which can then be placed within the host material as a discrete layer intermediate to adjacent layers of the host material(s).

In addition, imbibition of photochromic substances into a host material may be accomplished by the method described in U.K. Pat. Application No. 2,174,711, which is hereby incorporated in toto by reference. In that method a substantially mottle-free, substantially homogeneous film of polymeric resin having the photochromic substance dissolved therein is applied to the surface of the host material. The film-bearing host material is heated to temperatures near to but below the melting temperature of the photochromic substance for a time sufficient to incorporate a photochromic amount of the photochromic substance into the surface of the host. The photochromic-depleted film is then removed from the host surface with a suitable solvent.

Imbibition of photochromic substances into a host material, e.g., an ophthalmic lens, may be performed readily also by dissolving the photochromic substance in a suitable solvent, e.g., toluene, and absorbing the resulting solution into a temporary substrate, such as filter paper or other substrates described in subparagraph (d) above. The concentration of the photochromic substance in the solvent may vary and will depend on the solubility of the substance in the solvent used. Suitably, the photochromic substance will be present in the solvent at a concentration of from about 5 to 15, e.g., 10, weight percent. The temporary substrate may be a flexible material that can take the shape of the surface of the host material on which it is placed if such surface is irregular or not flat, such as the curved surface of the lens.

The temporary substrate containing the solution of photochromic substances is dried to remove the solvent and the substrate placed in contact with the surface of the host material. Optionally, a metal cap having the shape of the host material surface is placed on top of the temporary substrate to insure uniform contact of the interface of the substrate and host surface. For example, when the host is a lens, the cap and temporary substrate should be shaped to conform to the shape of the lens, e.g., the convex or concave surface of the lens. This sandwich comprising the metal cap-temporary substrate-host material is then heated for a time sufficient to imbibe a photochromic amount of the photochromic substance(s) into the subsurface of the host material. Heating times may range from about 15 minutes to 180 minutes, usually from 45 to 120 minutes at transfer temperatures, which may range from 125° C. to 155° C.

The aforesaid process may be repeated one or more times, e.g., two or three times, to imbibe the desired amount of photochromic substance into the subsurface of the host material, e.g., to a depth beneath the surface of up to about 50 microns. In the case of semi-finished lenses, the imbibition process is performed on the front (convex) surface of the lens to allow finishing (grinding) of the back (concave) surface. Further, the edges of the lens may be ground to remove imperfections before thermally transferring the photochromic substances. If desired, the host material may then be tinted with a color compatible dye e.g., a brown, yellow-brown or gray dye.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance. i.e., so the change in color is readily apparent to the observer. Preferably, the host material article is a solid transparent or optically clear material, e.g., materials suitable for optical applications, such as plano and ophthalmic lenses, windows, automotive transparencies, e.g., windshields, aircraft transparencies, plastic sheeting, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethan having terminal diacrylate functionality, as described in U.S. Pat. No. 4,360,653, cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., U.S. Pat. Nos. 2,370,567 and 2,403,113.

The aforedescribed polyol (allyl carbonate) monomers may be represented by the graphic formula:

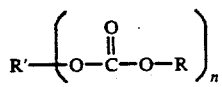
(VIII)

wherein R is the radical derived from an unsaturated alcohol and is commonly an allyl or substituted allyl group, R' is the radical derived from the polyol, and n is a whole number from 2 –5, preferably 2. The allyl group (R) may be substituted at the 2 position with a halogen, most notably chlorine or bromine, or an alkyl group containing from 1 to 4 carbon atoms, generally a methyl or ethyl group. The R group may be represented by the graphic formula:

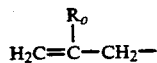
(IX)

wherein $R_o$ is hydrogen, halogen, or a $C_1$–$C_4$ alkyl group. Specific examples of R include the groups: allyl, 2-chloroallyl, 2-bromoallyl, 2-fluoroallyl, 2-methylallyl, 2-ethylallyl, 2-isopropylallyl, 2-n-propylallyl, and 2-n-butylallyl. Most commonly R is the allyl group, $H_2C=CH—CH_2—$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

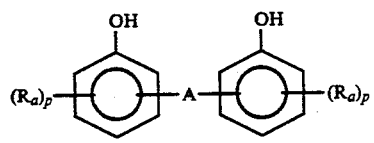
(X)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), $R_a$ represents lower alkyl substituents of from 1 to 3 carbon atoms and halogen, e.g., chlorine and bromine, and p is 0, 1, 2, or 3. Preferably, the hydroxyl group is in the ortho or para position.

Specific examples of the radical R' include: alkylene groups containing from 2 to 10 carbon atoms such as ethylene, (—$CH_2$—$CH_2$—), trimethylene, methylethylene, tetramethylene, ethylethylene, pentamethylene, hexamethylene, 2-methylhexamethylene, octamethylene, and decamethylene; alkylene ether groups such as —$CH_2$—O—$CH_2$—, —$CH_2CH_2$—(O—$CH_2$—)—$CH_2$—, —$CH_2$—(O—$CH_2$—)—$CH_2$—, and —$CH_2CH_2$—$CH_2$—O—$CH_2CH_2CH_2$—; alkylene polyether groups such as —$CH_2CH_2$—O—$CH_2CH_2$—O—$CH_2CH_2$—, and —$CH_2CH_2CH_2$—O—$CH_2CH_2$—$CH_2$—O—$CH_2CH_2CH_2$—; alkylene carbonate and alkylene ether carbonate groups such as —$CH_2$—$CH_2$—O—CO—O—$CH_2CH_2$— and —$CH_2$—$CH_2$—O—$CH_2CH_2$—O—CO—O—$CH_2$—$CH_2$—O—$CH_2CH_2$—; and isopropylidene bis(para-phenyl),

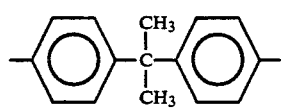
(XI)

Most commonly, R' is —$CH_2CH_2$—, —$CH_2$—$CH_2$—O—$CH_2$)$CH_2$—, or —$CH_2CH_2$—O—$CH_2CH_2$—O—$CH_2CH_2$—.

Specific non-limiting examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which may be utilized in the invention herein contemplated are:

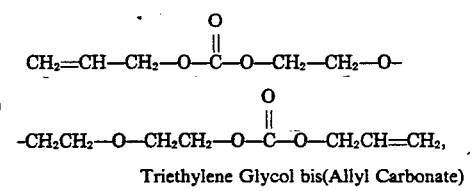
(XII)

Triethylene Glycol bis(Allyl Carbonate)

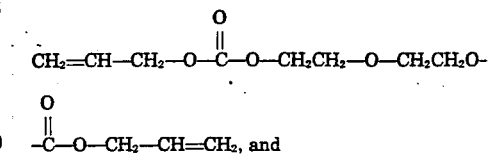
(XIII)

Diethylene Glycol bis(Allyl Carbonate)

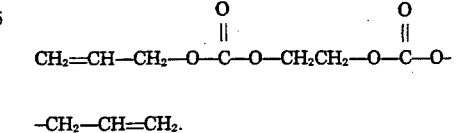
(XIV)

—$CH_2$—CH=$CH_2$.

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alco- alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

$$R-O-C(=O)-[O-R_b-O-C(=O)-]_s O-R \qquad (XV)$$

wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula, $$CH_2=CH-CH_2-O-C(=O)-[-O-CH_2-CH_2-O-CH_2-CH_2 \\ -O-C]_s-O-CH_2-CH=CH_2 \qquad (XVI)$$

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer, i.e., prepolymer, can be used. In that embodiment, the monomer is thickened by heating or partially polymerized by using small, e.g., 0.5-1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

$$(CH_2=C(R_t)-C(O))-_nR'' \qquad (XVII)$$

wherein $R_t$ is hydrogen or methyl, n is the number 2, 3, or 4, and $R''$ is the multivalent radical, i.e., a bivalent, trivalent or quadravalent radical, remaining after removal of the hydroxy groups from a polyol, having from 2 to 4 hydroxy groups, e.g., a diol, a triol or tetracarbinol respectively. More particularly, $R_t$ is hydrogen or methyl, and n is 2 or 3, more usually 2.

$R^2$ may be selected from the group consisting of alpha, omega $C_2$-$C_8$ glycols, cyclohexane diol, diethylene glycol, triethylene glycol, tetraethylene glycol, dipropylene glycol, $C_2$-$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethyacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2$=$CH-$) grouping. Such compatible monomers include monofunctional acrylic and methacrylic acid esters, and vinyl esters of $C_2$-$C_6$ carboxylic acids, i.e., vinyl carboxylates. Preferably, the copolymerizable monomer is a non-aromatic, e.g., non-benzenoid, containing monomer. Monofunctional acrylic or methacrylic ester monomers may be graphically illustrated by the following formula, $$CH_2=C(R_t)-C(O)-O-R''' \qquad (XVIII)$$

wherein $R_t$ is hydrogen or methyl, and $R'''$ is selected from the group consisting of $C_1$-$C_{12}$, e.g., $C_1$-$C_8$, alkyl, $C_5$-$C_y$ cycloalkyl, glycidyl and hydroxyethyl. Preferably, $R'''$, is a $C_1$-$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, 1, dl)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$-$C_6$ carboxylic acids, $C_1$-$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula XI.

The amount of photochromic substance or composition-containing same applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity. Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material.

The present invention is more particularly described in the following examples which are intended as illustrative only, since numerous modifications and variations therein will be apparent to those skilled in the art.

EXAMPLE 1

STEP 1

Anisole (5.4 grams, 0.05 mole) and aluminum chloride (8.4 grams, 0.06 mole) were mixed with 75 milliliters of carbon disulfide in a 250 milliliter round bottom flask. While cooling the flask in an ice bath, 2-fluorobenzoyl chloride (7.9 grams, 0.05 mole) was slowly added to the mixture in the reaction flask. The contents of the flask were stirred for one hour at room temperature and then poured into an equal volume of dilute aqueous hydrogen chloride. Methylene chloride (about 75 milliliters) was added to the reaction mixture and the resultant organic layer separated from the aqueous layer. Methylene chloride was separated from the recovered organic layer on a rotary evaporator. The residue, an oil, was dissolved in hexane and the hexane solution cooled to obtain a solid crystalline product (9.1 grams). A nuclear magnetic resonance (NMR) spectrum showed the solid crystalline product to be 2-fluoro-4'-methoxybenzophenone.

Step 2

The dry 2-fluoro-4'-methoxybenzophenone (9.1 grams, 0.039 mole) obtained in Step 1 was stirred at room temperature in 150 milliliters (ml) dry tetrahydrofuran in a reaction flask. A 10 molar percent excess of sodium acetylide in xylene/mineral oil was added to the reaction flask via pipet. The reaction mixture was stirred overnight at room temperature while being protected from atmospheric moisture by a nitrogen pad. The reaction mixture was poured into an equal volume of dilute aqueous hydrochloric acid and the organic phase separated. The aqueous phase was extracted with ether and the combined organic fractions dried over anhydrous sodium sulfate. The organic solvent (THF) was removed on a rotary evaporator to yield 13.9 grams of a crude oil product containing 1(2-fluorophenyl)-1-(4-methoxyphenyl) 2-propyn-1-ol, which was identified by NMR analysis.

Step 3

A portion of the crude oil product (6.95 grams) of Step 2 containing 1(2-fluorophenyl)-1-(4-methoxyphenyl)-2-propyn-1-ol was stirred in 150 milliliters benzene at room temperature with an excess of 2-naphthol (4.3 grams) plus a small catalytic amount of p-toluene sulfonic acid. After stirring for one hour, an NMR spectra of a small portion of the reaction mixture indicated no acetylenic alcohol was present. The reaction mixture was then poured into an equal volume of water. The organic fraction was washed twice with 50 milliliter portions of aqueous 5 percent sodium hydroxide solution to remove excess naphthol. The benzene solvent was removed on a rotary evaporator leaving an oil that was purified by chromatography. The photochromic fractions from the chromatographic purification were combined and crystallized from a hexane:ether mixture to yield 3.6 grams of the compound, 3(2-fluorophenyl)-3(4-methoxyphenyl)-3H-naphtho [2,1-b]pyran. The melting range of the product was found to be 104–105° C.

EXAMPLE 2

The procedure of Step 1 of Example 1 was followed except that veratrole (1,2-dimethoxybenzene) (6.9 grams, 0.05 mole) was substituted for anisole. The ketone, 2-fluoro-3',4'-dimethoxy benzophenone (9.5 grams) was obtained. The benzophenone melted at 85–87° C. The procedure of Step 2 of Example 1 was followed using 2-fluoro-3',4'-dimethoxybenzophenone in place of the 2-fluoro-4'-methoxybenzophenone of Example 1. The product was an oil which was chromatographed to yield the desired propargyl alcohol, which was crystallized from hexane. The melting range of the solid product was found to be 116–118° C. and was identified as 1(2-fluorophenyl)-1-(3,4-dimethoxyphenol)-2-propyn-1-ol (by NMR).

Two grams of the 1(2-fluorophenyl)-1-(3,4-dimethoxyphenol)-2-propyn-1-ol product was combined with 150 milliliters of toluene, 1.2 grams of 2-naphthol and 15 grams of acidic alumina. The mixture was stirred for 15 hours at 60° C. The alumina was filtered and washed several times with ethyl acetate until no more photochromic was extracted. The organic fractions were combined and the ethyl acetate solvent removed on a rotary evaporator leaving an oil that was chromatographed on silica using chloroform. The photochromic fractions were combined and crystallized from hexane to give 1.0 grams of the product, 3(2-fluorophenyl)-3(3,4-dimethoxyphenol)-3H-naphtho [2,1-b]pyran. The melting point range was 144–146° C.

2-methyl-4,4'-dimethoxybenzophenone was prepared from the Friedel-Crafts reaction of 3-methyl anisole with anisoyl chloride using aluminum chloride as catalyst and hexane as the solvent. The benzophenone product (6.1 grams, 0.02 mole) was converted to the propargyl alcohol according to the procedure of Example 1, Step 2. The resulting crude oil was taken up in 150 milliliters of benzene and 2.8 grams (0.01 mole) of 2-naphthol and 0.1 grams of p-toluene sulfonic acid were added to the benzene solution. The resulting mixture was stirred at room temperature for about 30 minutes and then poured into an equal volume of 5 percent aqueous sodium hydroxide. The organic layer was washed with water and the benzene solvent removed on a rotary evaporator. The remaining crude product was subjected to column chromatography using a 1:1 mixture of chloroform and hexane as elutant. The photochromic fractions were combined and the product crystallized from a mixture of hexane and ether. The product had a melting range of 112-114C. Nuclear Magnetic Resonance (NMR) analysis of the product confirmed it to be, 3(2-methyl-4-methoxyphenyl)-3-(4methoxyphenyl)-3H-naphtho-[2,1-b]pyran.

EXAMPLE 4

2-methyl-4'-methoxybenzophenone was prepared by the Friedel-Crafts reaction of ortho-toluoyl chloride and anisole using aluminum chloride as a catalyst and carbon disulfide as the solvent. 11.1 grams (0.05 mole) of the resulting benzophenone was converted to the propargyl alcohol using the method described in Example 1, Step 2. The crude product was mixed with 6 grams of 2-naphthol and 0.1 gram of p-toluene sulfonic acid in 200 milliliters of benzene and the mixture stirred overnight at room temperature. The resultant reaction mixture was poured into an equal volume of aqueous 5 percent sodium hydroxide to remove unreacted naphthol. The organic layer was washed with water and the benzene solvent removed on a rotary evaporator. The resulting oil residue was column chromatographed on silica using a 1:1 mixture of chloroform and hexane as elutant. The photochromic fractions were combined and the product crystallized from a mixture of hexane and diethyl ether. The product (4.8 grams) had a melting range of 131-133° C. NMR analysis of the product confirmed it to be 3(2-methylphenyl)-3-(4-methoxyphenyl)-3H-naphtho[2,1-b]pyran.

EXAMPLE 5

2,4-dimethoxybenzophenone was prepared by the Friedel-Crafts reaction of 1,3-dimethoxybenzene with benzoyl chloride in carbon disulfide using aluminum chloride as the catalyst 11.4 grams (0.05 mole) of the resulting benzophenone was converted to the propargyl alcohol using the conditions described in Example 1, Step 2. The crude propargyl alcohol was taken up in 150 milliliters of toluene. 3 grams (0.02 mole) of 2-naphthol and 30 grams of anhydrous acidic alumina were added to the toluene solution. The resulting slurry was refluxed for 3 hours, cooled and filtered. The alumina was separated from the reaction mixture and washed with toluene until no more photochromic was extracted therefrom. The solvent solutions were combined and the toluene solvent removed on a rotary evaporator. The residue was chromatographed on silica using a 4:1 mixture of hexane and ethyl acetate as elutant. The photochromic fractions were combined and rechromatographed using a 3:7 mixture of hexane and chloroform as elutant. The photochromic product readily crystallized from hexane. 2.6 grams of crystallized product having a melting range of 132-134° C. were obtained. NMR analysis of the product confirmed it to be 3-phenyl-3-(2,4-dimethoxyphenyl)-3H-naphtho[2,1-b]pyran.

EXAMPLE 6

2,6-difluoro-4'-methoxybenzophenone was prepared by Friedel-Crafts reaction of 2,6-difluorobenzoyl chloride with anisole in carbon disulfide using aluminum chloride as catalyst. 4.8 grams (0.02 mole) of the benzophenone was converted to the propargyl alcohol using the conditions described in Example 1, Step 2. The crude propargyl alcohol was taken up in 200 milliliters of benzene and 3.0 grams (0.02 mole) of naphthol and 0.1 grams of p-toluene sulfonic acid catalyst was added to the benzene solution. After stirring for 1 hour, the reaction mixture was poured into an equal volume of 5 percent aqueous sodium hydroxide. The organic layer was separated and the benzene solvent removed on a rotary evaporator. The residue was chromatographed on silica using a 4:1 mixture of hexane:ethyl acetate as elutant. The photochromic fractions were collected and crystallized from n-propanol. 1.2 grams of product having a melting range of 122-124° C. was obtained. NMR analysis confirmed the product to be 3(2,6-difluorophenyl)-3(4-methoxyphenyl)-3H- naphtho[2,1-b]pyran.

COMPARATIVE EXAMPLE 1

To a 500 milliliter reaction flask were added 0.1 mole (20.8 grams) of 1,1-diphenyl-2-propyn-1-ol, 15 grams of 2-naphthol and 200 milliliters of benzene. The reaction mixture was warmed to 55° C. to dissolve all of the naphthol reactant. When all of the 2-naphthol was dissolved, 0.25 grams of p-toluene sulfonic acid was added to the stirred reaction mixture, which then changed from light tan to dark black and exothermed to 70° C. After a few minutes, the reaction mixture lightened and began to cool. After 30 minutes, the reaction mixture was poured into 100 milliliters of 10 percent aqueous sodium hydroxide and shaken. The organic phase was washed once with 10 percent aqueous sodium hydroxide and then washed with water. The benzene solvent was removed on a rotary evaporator. The resulting solid residue was a light tan solid, which was slurried with 100 milliliters of hexane and then filtered. The filtered solid was washed again with 100 milliliters of hexane and dried to provide 18.4 grams of the product, 3,3-diphenyl-3H-naphtho[2,1-b]pyran, which was found to be 98 percent pure by HPLC. The product had a melting point range of 156-158° C.

COMPARATIVE EXAMPLE 2

Anisole (0.1 mole, 10.8 grams) and benzoyl chloride (0.1 mole, 14 grams) were dissolved in 200 milliliters of hexane and stirred at room temperature while 15 grams of anhydrous aluminum chloride were added slowly over a period of 15 minutes. The reaction mixture was stirred an additional 15 minutes and then the hexane decanted. The resulting viscous residue in the reaction flask was carefully hydrolyzed with 200 milliliters of a mixture of ice and dilute hydrochloric acid. The resulting organic fraction was taken up in dichloromethane and the resulting solution washed with water. Dichloromethane solvent was removed on a rotary evaporator leaving an oil product that solidified on standing. The solidified product was broken-up and washed with two 50 milliliters portions of pentane. Suction drying afforded 4-methoxybenzophenone in near quantitative yield.

10 grams of this 4-methoxybenzophenone was converted to the propargyl alcohol by the procedure described in Example 1, Step 2. NMR analysis of the resulting product showed it to be a mixture of 1-phenyl-1(4-methoxyphenyl)-2-propyn-1-ol and the starting ketone, 4-methoxybenzophenone, in a ratio of 3:1.

The crude propargyl alcohol was added to a slurry of 5 grams of 2-naphthol, 40 grams of anhydrous acid alumina and 200 milliliters of toluene. The resulting reaction mixture was heated to reflux for 30 minutes, cooled and filtered. The alumina was washed two times with 100 milliliter portions of hexane. The toluene and hexane fractions were combined and the organic solvents removed on a rotary evaporator. The resulting product was an orange oil that crystallized from a mixture of hexane and diethyl ether. The product crystals were washed with diethyl ether and dried to give 1.4 grams of a product having a melting range of 149-150° C. NMR analysis confirmed the product to be 3-phenyl-3(4-methoxyphenyl)-3H-naphtho[2,1-b]pyran.

COMPARATIVE EXAMPLE 3

4-methyl-4'methoxybenzophenone was prepared from anisole and p-toluoyl chloride using the procedure described in Comparative Example 2. The resulting ketone was converted to the propargyl alcohol and then reacted with 2-naphthol as in Comparative Example 2 to produce 2.1 grams of light yellow crystals having a melting range of 146-147° C. NMR analysis confirmed the product to be 3(4-methylphenyl)-3-(4-methoxyphenyl)-3H-naphtho[2,1-b]pyran.

COMPARATIVE EXAMPLE 4

4-(trifluoromethyl)benzophenone (7.5 grams, 0.03 mole) and 9.6 grams (0.36 mole) of an 18% slurry of sodium acetylide in xylene/light mineral oil were stirred in 125 ml of dry tetrahydrofuran overnight. The mixture was protected from moisture by a nitrogen pad. The next day the solution was poured into cold dilute hydrochloric acid. The organic fraction was taken up in methylene chloride, washed with water and dried over sodium sulfate. Evaporation of the solvents yielded 12.6 grams of a crude oil. NMR analysis of the crude oil confirmed it to be the desired 1-phenyl-1-(4-trifluoromethylphenyl)-2-propyn-1-ol.

6.2 grams of the crude oil (about 0.015 mole) and 2.6 grams (0.018 mole) of 1-naphthol were mixed in 200 ml of toluene with 30 grams of dry acidic alumina. The mixture was refluxed overnight and then filtered to remove the alumina. The alumina was washed with fresh toluene until no more photochromic was extracted. The combined toluene fractions were washed with dilute sodium hydroxide to remove excess naphthol. The toluene solvent was then removed on a rotary evaporator and the crude oil column chromatographed on silica using a 9:1 mixture of hexane:ethylacetate as elutant. The photochromic fractions were combined and rechromatographed on silica using a 2:1 mixture of hexane:chloroform as elutant. The photochromic fractions were combined to yield 1.5 grams of an oil which was 98.9% pure by HPLC analysis. NMR analysis confirmed the product to be 3-phenyl-3(4-trifluoromethylphenyl)-2H-naphtho[1,2-b]pyran.

COMPARATIVE EXAMPLE 5

1,1-di(3-trifluoromethyl)phenyl-2-propyn-1-ol (about 13 grams) was prepared from 3,3'-bis(trifluoromethyl)-benzophenone (0.03 mole) by the method described in Comparative Example 4. Half of the oil product was mixed with 200 ml of toluene and 2.88 grams (0.02 mole) of 1-naphthol. 30 grams of dry acidic alumina was added and the mixture refluxed overnight. The reaction mixture was filtered and the alumina washed with fresh toluene until no more photochromic was extracted. The toluene fractions were combined, washed with dilute sodium hydroxide to remove excess naphthol, and the toluene removed on a rotary evaporator. The resulting oil was chromatographed on silica using a 9:1 mixture of hexane:ethylacetate as elutant. 3.5 rams of a solid was obtained. The solid product was recrystallized from hexane to give 0.8 grams of a solid having a melting range of 121° C.-123° C. The product was found to be 98.6% pure by HPLC analysis. NMR analysis confirmed the product to be 3,3-di(3-trifluoromethyl)phenyl-2H-naphtho [1,2-b]pyran.

Naphthopyran compounds prepared in the above-described Examples were imbibed by thermal transfer into test samples of a homopolymer of diethylene glycol bis(allyl carbonate) by the following procedure. Each naphthopyran was dissolved into toluene solvent to form a 4% solution of the compound. A piece of No. 4 Whatman filter paper was saturated with the naphthopyran solution and allowed to air dry. The dried filter paper was placed on one side of the polymer test sample, which measured ⅛ inch (0.3 centimeter)×2 inch (5.1 centimeters)×2 inch (5.1 centimeters). A piece of untreated filter paper was placed on the other side of the polymer test sample and the resulting sandwich placed between two plates of flat aluminum metal plates. The entire assembly was then placed in a 155° C. oven for a time sufficient to thermally transfer the naphthopyran into the polymer test sample. Residence times in the oven were adjusted to imbibe comparable amounts of the naphthopyran compounds, as measured by UV absorbance.

The imbibed test samples were removed from the oven, washed with acetone, and tested for photochromic response rates on an optical bench. The samples were illuminated by a 150 watt Xenon lamp fitted with a copper sulfate bath and neutral density filter at an intensity of about one sun. The optical density at saturation was determined at twenty minutes exposure. Results are tabulated in Table 4.

TABLE 4

| | Δ OD at SATURATION | Bleach Rate T½ (sec.) |
|---|---|---|
| COMPOUND EXAMPLE | | |
| 1 | 1.00 | 170 |
| 2 | 1.05 | 203 |
| 3 | 1.35 | 510 |
| 4 | 2.40 | 600 |
| 5 | 1.42 | 510 |
| 6 | 2.23 | >30 minutes |
| COMPARATIVE EXAMPLE | | |
| 1 | 0.36 | 45 |
| 2 | 0.25 | 35 |
| 3 | 0.21 | 40 |
| 4 | 1.63 | >30 minutes |
| 5 | 1.07 | >30 minutes |
| a. | 1.37 | >30 minutes | a. Purchased 2,2-diphenyl-2H naphthol[1,2-b]pyran

The data of Table 4 show that naphthopyran compounds derived from 2-naphthol and having an ortho-substituted phenyl substituent at the 3-position of the pyran ring have reasonable decolorization rates; those having two ortho-substituted phenyl substituents have a high activated intensity but longer decolorization rates. Naphthopyran compounds derived from 2-naphthol, which do not have an ortho-substituted phenyl substituent bleach very rapidly, while naphthopyran compounds derived from 1-naphthol have long decolorization rates.

Although the present invention has been described with reference to the specific details of particular embodiments thereof, it is not intended that such details be regarded upon the scope of the invention except insofar as to the extent that they are included in the accompanying claims.

We claim:

1. A naphthopyran compound represented by the following graphic formula:

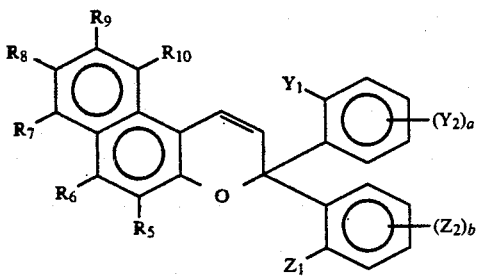

wherein $Y_1$ is selected from the group consisting of $C_1$–$C_5$ alkyl, $C_1$–$C_5$ alkoxy, fluoro and chloro; $Z_1$ is selected from the group consisting of hydrogen and $Y_1$; $Y_2$ and $Z_2$ are each selected from the group consisting of $C_1$–$C_5$ alkyl, $C_1$–$C_5$ alkoxy, cyano, hydroxy, halogen, acrylyl, methacrylyl, acryloxy ($C_1$–$C_4$) alkyl and methacryloxy ($C_1$–$C_4$) alkyl; a and b are each integers selected from the group consisting of 0, 1 and 2; and $R_5$–$R_{10}$ are each selected from the group consisting of hydrogen, $C_1$–$C_{10}$ alkyl, $C_5$–$C_7$ cycloalkyl, phenyl, mono- or di- substituted phenyl, $C_1$–$C_4$ alkoxy, halogen, acrylyl, methacrylyl, acryloxy ($C_1$–$C_4$) alkyl, methacryloxy ($C_1$–$C_4$) alkyl, furyl and thienyl, said phenyl substituents being selected from the group consisting of $C_1$–$C_4$ alkyl, $C_1$–$C_4$ alkoxy, chloro and bromo.

2. A naphthopyran compound according to claim 1 wherein $Y_1$ is selected from the group consisting of $C_1$–$C_3$ alkyl, $C_1$–$C_3$ alkoxy and fluoro; $Z_1$ is selected from the group consisting of hydrogen and $Y_1$; $Y_2$ and $Z_2$ are each selected from the group consisting of $C_1$–$C_3$ alkyl, $C_1$–$C_3$ alkoxy and fluoro; a and b are each integers selected from the group consisting of 0, 1 and 2; and $R_5$–$R_{10}$ are each selected from the group consisting of hydrogen, $C_1$–$C_5$ alkyl, $C_5$–$C_6$ cycloalkyl, $C_1$–$C_3$ alkoxy, chloro, bromo, 2-furyl, 3-furyl, 2-thienyl, 3-thienyl, phenyl, ortho-, meta- or para- substituted phenyl, said phenyl substituents being selected from the group consisting of $C_1$–$C_4$ alkyl, $C_1$–$C_4$ alkoxy, chloro and bromo.

3. A naphthopyran compound according to claim 2 wherein the $R_5$–$R_{10}$ substituted phenyl substituent is a para-substituted phenyl.

4. A naphthopyran compound according to claim 2 wherein $R_5$–$R_{10}$ are each selected from the group consisting of hydrogen $C_1$–$C_3$ alkyl, $C_1$–$C_3$ alkoxy, chloro, bromo, phenyl and $C_1$–$C_3$ alkoxyphenyl.

5. A naphthopyran compound according to claim 4 wherein the $C_1$–$C_3$ alkoxyphenyl is a para $C_1$–$C_3$ alkoxyphenyl.

6. A naphthopyran compound according to claim 2 wherein $R_5$–$R_{10}$ are each hydrogen.

7. A naphthopyran compound according to claim 2 wherein $R_5$–$R_9$ are each hydrogen, $R_5$–$R_8$ are each hydrogen, or $R_5$ and $R_7$–$R_9$ are each hydrogen.

8. A naphthopyran compound according to claim 2 wherein $Y_1$ is selected from the group consisting of $C_1$–$C_3$ alkyl, $C_1$–$C_3$ alkoxy and fluoro; $Z_1$ is hydrogen; $Y_2$ is $C_1$–$C_3$ alkoxy; $Z_2$ is selected from the group consisting of $C_1$–$C_3$ alkyl and $C_1$–$C_3$ alkoxy; $R_5$–$R_{10}$ are each hydrogen, a is the integer 0 or 1 and b is the integer 0, 1 or 2.

9. A naphthopyran compound according to claim 8 wherein when a or b are the integer 1, the $Y_2$ and $Z_2$ substituents are located at the 3, 4 or 5 carbon atom position.

10. A naphthopyran compound according to claim 9 wherein the $Y_2$ and $Z_2$ substituents are located at the 3 or 4 carbon atom position.

11. A naphthopyran compound according to claim 8 wherein when b is 2, the $Z_2$ substituents are located at the 3 and 4, 3 and 5 or 4 and 5 carbon atom positions.

12. 3(2-fluorophenyl)-3(4-methoxyphenyl)-3H-naphtho[2,1-b]pyran.

13. 3(2-fluorophenyl)-3(3,4-dimethoxyphenyl)-3H-naphtho[2,1-b]-pyran.

14. 3(2-methyl-4-methoxyphenyl)-3(4-methoxyphenyl)-3H-naphtho [2,1-b]pyran.

15. 3(2-methylphenyl)-3(4-methyloxphenyl)-3H-naphtho[2,1-b]pyran.

16. 3-phenyl-3(2,4-dimethoxyphenyl)-3H-naphtho[2,1-b]pyran.

17. A photochromic article comprising a polymerized organic host material and a photochromic amount of a naphthopyran compound represented by the following graphic formula:

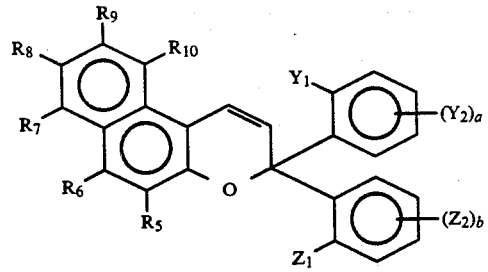

wherein $Y_1$ is selected from the group consisting of $C_1$–$C_5$ alkyl, $C_1$–$C_5$ oxy, fluoro and chloro; $Z_1$ is selected from the group consisting of hydrogen and $Y_1$; $Y_2$ and $Z_2$ are each selected from the group consisting of $C_1$–$C_5$ alkyl, $C_1$–$C_5$ alkoxy, cyano, hydroxy, halogen, acrylyl, methacrylyl, acryloxy ($C_1$–$C_4$) alkyl and methacryloxy ($C_1$–$C_4$) alkyl; a and b are each integers selected from the group consisting of 0, 1 and 2; and $R_5$–$R_{10}$ are each selected from the group consisting of hydrogen, $C_1$–$C_{10}$ alkyl, $C_5$–$C_7$ cycloalkyl, phenyl, mono- or di- substituted phenyl, $C_1$–$C_4$ alkoxy, halogen, acrylyl, methacrylyl, acryloxy ($C_1$–$C_4$) alkyl, methacryloxy ($C_1$–$C_4$) alkyl, furyl and thienyl, said phenyl substituents being selected from the group consisting of $C_1$–$C_4$ alkyl, $C_1$–$C_4$ alkoxy, chloro and bromo.

18. The photochromic article of claim 17 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

19. The photochromic article of claim 18 wherein $Y_1$ is selected from the group consisting of $C_1$–$C_3$ alkyl, $C_1$–$C_3$ alkoxy and fluoro; $Z_1$ is selected from the group consisting of hydrogen $Y_2$ and $Z_2$ are each selected from the group consisting of $C_1$–$C_3$ alkyl, $C_1$–$C_3$ alkoxy and fluoro; a and b are each integers selected from the group consisting of 0, 1 and 2; and $R_5$–$R_{10}$ are each selected from the group consisting of hydrogen, $C_1$–$C_5$ alkyl, $C_5$–$C_6$ cycloalkyl, $C_1$–$C_3$ alkoxy, chloro, bromo, 2-furyl, 3-furyl, 2-thienyl, 3-thienyl, phenyl, and ortho-, meta- or para- substituted phenyl, said phenyl substituents being selected from the group consisting of $C_1$–$C_4$ alkyl, $C_1$–$C_4$ alkoxy, chloro and bromo.

20. The photochromic article of claim 19 wherein $Y_1$ is selected from the group consisting of $C_1$–$C_3$ alkyl, $C_1$–$C_3$ alkoxy and fluoro; $Z_1$ is hydrogen; $Y_2$ is $C_1$–$C_3$ alkoxy; $Z_2$ is selected from the group consisting of $C_1$–$C_3$ alkyl and $C_1$–$C_3$ alkoxy; $R_5$–$R_{10}$ are each hydrogen, a is the integer 0 or 1 and b is the integer 0, 1 or 2.

21. The photochromic article of claim 20 wherein the organic host material is a solid transparent homopolymer or copolymer of diethylene glycol bis(allyl carbonate), poly(4,4'-dioxydiphenol-2,2-propane), polymethylmethacrylate, or polyvinylbutyral.

22. The photochromic article of claim 21 wherein the photochromic compound is present in an amount of from about 0.01 to 20 weight percent.

23. The photochromic article of claim 22 wherein the article is a lens.

24. The photochromic article comprising a solid transparent polymerized organic host material and a photochromic amount of each of (a) a first photochromic substance selected from the group consisting of spiro-(indolino) naphthoxazines, spiro(indolino) pyrido benzoxazines, and spiro(indolino) benzoxazines, and (b) a naphthopyran compound represented by the following graphic formula:

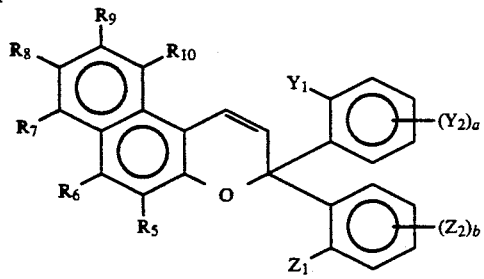

wherein $Y_1$ is selected from the group consisting of $C_1$–$C_5$ alkyl, $C_1$–$C_5$ alkoxy, fluoro and chloro; $Z_1$ is selected from the group consisting of hydrogen and $Y_1$; $Y_2$ and $Z_2$ are each selected from the group consisting of $C_1$–$C_5$ alkyl, $C_1$–$C_5$ alkoxy, cyano, hydroxy, halogen, acrylyl, methacrylyl, acryloxy ($C_1$–$C_4$) alkyl and methacryloxy ($C_1$–$C_4$) alkyl; a and b are each integers selected from the group consisting of 0, 1 and 2; and $R_5$–$R_{10}$ are each selected from the group consisting of hydrogen, $C_1$–$C_{10}$ alkyl, $C_5$–$C_7$ cycloalkyl, phenyl, mono- or di- substituted phenyl, $C_1$–$C_4$ alkoxy, halogen, acrylyl, methacrylyl, acryloxy ($C_1$–$C_4$) alkyl, methacryloxy ($C_1$–$C_4$) alkyl, furyl and thienyl, said phenyl substituents being selected from the group consisting of $C_1$–$C_4$ alkyl, $C_1$–$C_4$ alkoxy, chloro and bromo.

25. The photochromic article of claim 24 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

26. The photochromic article of claim 25 wherein $Y_1$ is selected from the group consisting of $C_1$–$C_3$ alkyl, $C_1$–$C_3$ alkoxy and fluoro; $Z_1$ is selected from the group consisting of hydrogen and $Y_1$; $Y_2$ and $Z_2$ are each selected from the group consisting of $C_1$–$C_3$ alkyl, $C_1$–$C_3$ alkoxy and fluoro; a and b are each integers selected from the group consisting of 0, 1 and 2; and $R_5$–$R_{10}$ are each selected from the group consisting of hydrogen, $C_1$–$C_5$ alkyl, $C_5$–$C_6$ cycloalkyl, $C_1$–$C_3$ alkoxy, chloro, bromo, 2-furyl, 3-furyl, 2-thienyl, 3-thienyl, phenyl, and ortho-, meta- or para- substituted phenyl, said phenyl substituents being selected from the group consisting of $C_1$–$C_4$ alkyl, $C_1$–$C_4$ alkoxy, chloro and bromo.

27. The photochromic article of claim 26 wherein $Y_1$ is selected from the group consisting of $C_1$–$C_3$ alkyl, $C_1$–$C_3$ alkoxy and fluoro; $Z_1$ is hydrogen; $Y_2$ is $C_1$–$C_3$ alkoxy; $Z_2$ is selected from the group consisting of $C_1$–$C_3$ alkyl and $C_1$–$C_3$ alkoxy; $R_5$–$R_{10}$ are each hydrogen, a is the integer 0 or 1 and b is the integer 0, 1 or 2.

28. The photochromic article of claim 27 wherein the organic host material is a solid transparent homopolymer or copolymer of diethylene glycol bis(allyl carbonate), poly(4,4'-dioxydiphenol-2,2-propane), polymethylmethacrylate, or polyvinylbutyral.

29. The photochromic article of claim 27 wherein the first photochromic substance is a spiro(indolino) pyrido benzoxazine or spiro(indolino) naphthoxazine.

30. The photochromic article of claim 27 wherein the first photochromic substance is a spiro(indolino) benzoxazine.

31. The photochromic article of claim 26 wherein the first photochromic substance and photochromic naphthopyran compound are each present in amounts of from about 0.05 to about 10 weight percent.

32. The photochromic article of claim 33 wherein the weight ratio of the first photochromic substance to the naphthopyran compound varies from about 1:3 to about 3:1.

33. The photochromic article of claim 32 wherein the article is an ophthalmic lens.

* * * * *

UNITED STATES PATENT AND TRADEMARK OFFICE
CERTIFICATE OF CORRECTION

PATENT NO. : 5,066,818

DATED : Nov. 19, 1991

INVENTOR(S) : Barry V. Gemert et al

It is certified that error appears in the above-identified patent and that said Letters Patent is hereby corrected as shown below:

Title page, item [75], "Barry V. Gemert" should be
--Barry Van Gemert--.

Claim 17, column 28, line 59, "oxy" should be --alkoxy--.

Claim 19, column 29, line 20, after "hydrogen" insert --and $Y_1$;--.

Signed and Sealed this

First Day of June, 1993

Attest:

MICHAEL K. KIRK

*Attesting Officer*     *Acting Commissioner of Patents and Trademarks*